United States Patent [19]

Liedtke

[11] Patent Number: 5,686,112
[45] Date of Patent: Nov. 11, 1997

[54] SINGLE DOSAGE SEMI-SOLID TOPICAL PHARMACEUTICAL FORMS FOR TRANSDERMAL THERAPY

[75] Inventor: Rainer K. Liedtke, Munich, Germany

[73] Assignee: APL-American Pharmed Labs, Inc., West Caldwell, N.J.

[21] Appl. No.: 569,958

[22] Filed: Dec. 20, 1995

Related U.S. Application Data

[63] Continuation of Ser. No. 82,939, Jun. 29, 1993, abandoned.

[30] Foreign Application Priority Data

Jul. 13, 1992 [DE] Germany ............... 42 23 004.7

[51] Int. Cl.⁶ ..................................... A61K 9/14
[52] U.S. Cl. .................... 424/489; 424/449; 424/444; 424/455; 424/478; 424/490
[58] Field of Search .................. 424/489, 444, 424/455, 478, 490, 449

[56] References Cited

U.S. PATENT DOCUMENTS

| | | | |
|---|---|---|---|
| 4,927,687 | 5/1990 | Nuwayser | 424/449 |
| 5,232,703 | 8/1993 | Blank | 424/449 |
| 5,234,957 | 8/1993 | Mantelle | 514/772.6 |

Primary Examiner—Thurman K. Page
Assistant Examiner—William E. Benston, Jr.
Attorney, Agent, or Firm—Oblon, Spivak, McClelland, Maier & Neustadt, P.C.

[57] ABSTRACT

To improve the efficacy and tolerability of customary topical applications for transdermal systemically acting pharmaceutical substances, single dosage topical pharmaceutical forms which are therapeutically exactly ready-to-administer are formed from suitable semi-solid pharmaceutical forms. The topical single doses are specified pharmaceutically with respect to their dose, their topical spreading behaviour and their permeation properties. Several of the topically ready-to-administer single doses are in this case accommodated in a common commercial packaging container. Complex treatments can be developed by means of different individual dosages or alternatively active compound combinations. As pharmacological active compounds, steroids, peptides, various analgesics, local anaesthetics and non-steroidal anti-rheumatics are employed in particular. The single dosage topical pharmaceutical form is a safe, easy to administer and inexpensive application form which makes possible a more exact topical therapy for systemic administrations than could previously be achieved using conventional topical administration forms.

15 Claims, 3 Drawing Sheets

SINGLE DOSAGE SEMI-SOLID TOPICAL PHARMACEUTICAL FORMS FOR TRANSDERMAL THERAPY

This application is a Continuation of application Ser. No. 08/082,939, filed on Jun. 29, 1993, now abandoned.

The invention relates to single dosage semi-solid topical pharmaceutical forms for transdermal therapy, in particular for improving the efficacy and tolerability of systemically acting pharmaceutical substances.

It is known that pharmaceutical substances are also applied to the skin. This is mainly carried out to achieve local effects, but in rarer cases also for systemically affecting bodily functions.

The latter is in particular the administration of topical semi-solid pharmaceutical forms, in particular of ointments, gels and creams, but recently preferably the administration of so-called transdermal therapeutic systems, commercially specified plaster systems which are already employed successfully for the treatment of various disorders.

Transdermal therapy with pharmaceutically customary semi-solid topical administration forms, e.g. in the sex steroid field, and also the transdermal administration of nitroglycerine could previously not be therapeutically successful, however, since the administration of these formulations could previously not be adequately directed to the requirements of a systemic transdermal therapy, in particular due to a lack of dosage accuracy and problems with practical handling. Topical administration of nitroglycerine by means of a spray was also commercially unsuccessful.

On the other hand, therapeutic transdermal systems in the meantime found very wide application, in particular in hormone replacement therapy for the treatment of postmenopausal symptoms and osteoporosis and, with nitroglycerine, as a symptomatic treatment of angina pectoris in coronary heart disease. Recent developments in this field are also aimed at the treatment of pain, e.g. transdermal systems containing the analgesic fentanyl, and at curing smokers, e.g. using transdermal nicotine plasters. Various transdermal application areas, e.g. transdermal scopolamine for the treatment of travel sickness and transdermal clonidine for the treatment of hypertension, also led, however, to controversial views on the benefit/risk ratio.

Customary pharmaceutical topical pharmaceutical forms show essentially relatively great inaccuracy in dosage as transdermal systems. Apart from pharmaceutical differences in the formulations themselves, this can mainly be traced back to the hitherto inconvenient and commercially crude administration technique. Thus, in this connection, only very rough and, from a subjective point of view, estimated volumes are administered from the containers, mainly tubes, partly with the aid of spatulas using a measuring scale. The volume dosage is in this case also still carried out by the patients themselves.

This procedure is only suitable, if at all, for relatively unspecific local therapies, e.g. in the treatment of local contusions with analgesics. Significant dosage problems also result with sprays, since with these not only the accurate release of the dose from the container itself, but also the appropriate topical surface coating is problematical. This is partly already caused, inter alia, by poorly controllable atomisation effects in the air, and partly also by ricochet effects on the skin.

Moreover, this type of intervention also requires special adhesive additives, which raise dermatotoxicological questions.

Transdermal systems are substantially more accurate, but on the other hand also very much more complicated and consequently expensive in terms of production. Furthermore, transdermal systems also frequently exhibit skin irritation, which is produced by the skin occlusion of the plaster necessary for this technique. Moreover, the transdermal systems are also designed for relatively long administration periods of several days, often for reasons of cost. The known transdermal systems are also more fixed to given constant active compound liberation rates, which usually approach zero order release kinetics, and thus correspond to the kinetics of an infusion. As is to be expected biologically, with some active compounds this leads to pharmacological habituation reactions. A practical example here is transdermal nitroglycerine, in which this leads to reproducible tachyphylaxis, by which on repeated administration the antianginal effects are reduced even short-term, in spite of a further increased dose, up to loss of action. For these cases, either undulating first order kinetics or, occasionally, interruptions of therapy in which the patients thus remain untreated, are the present means of choice for restoration of the activity.

For a topical transdermal therapy of systemic disease states, both sufficiently exact local dosage and the type of the administration scheme are thus both to be taken into account.

Lastly, for patient and physician a type of administration is also important which is suitable to carry out in practice and which avoids preparations which are too complex and thus an adequate readiness of the administration form for application. Furthermore, economical aspects with respect to the costs of a pharmaceutical therapy are also important. This applies in particular to chronic administrations.

The invention is based on the object of improving the efficacy and tolerability of topical administration for transdermal therapy for systemically acting pharmaceutical substances.

This object is achieved according to the invention by the pharmaceutical substances being present as therapeutically ready-to-administer topical individual doses of a suitable semi-solid pharmaceutical form, preferably a cream, emulsion, gel, suspension or ointment, or as therapeutically ready-to-administer topical individual doses of a further pharmaceutical modification of the same semi-solid pharmaceutical form, and the therapeutically ready-to-administer topical individual doses being situated in separate containers of a common commercial moulded body, which simultaneously serves as a pack for several therapeutically ready-to-administer topical individual doses, it being possible for the active compounds to be present in the therapeutically ready-to-administer topical individual doses either in various dosages, on their own, or in active compound combinations.

To improve the efficacy and tolerability of transdermal administrations of a systemic treatment, the active compounds contained in the pharmaceutical vehicle can in this case be present either in a specific average uniform crystal size or alternatively in mixtures having various crystal sizes.

To improve the efficacy and tolerability of transdermal administrations of a systemic treatment with steroids, in a further embodiment of the invention, as active compounds, oestrogens and gestagens or glucocorticoids are present as individual substances or in combinations in the single dosage topical pharmaceutical form.

To improve the efficacy and tolerability of transdermal administrations of a systemic treatment with peptides, in a further embodiment of the invention pharmacologically active peptides and proteins, in particular insulin, oxytocin or encephalins, are present as individual substances or in combinations in the single dosage topical pharmaceutical form.

To improve the efficacy and tolerability of a transdermal systemic pain or rheumatism treatment, in a further embodiment of the invention analgesics and local anaesthetics such as buprenorphine, fentanyl, penzocaine, morphine and morphine derivatives, lidocaine, prilocaine, mepivacaine or non-steroidal antirheumatics/antiinflammatories such as indomethacin, diclofenac or etofenamate are present as individual substances or in combinations in the single dosage topical pharmaceutical form.

To improve the efficacy and tolerability of a transdermal systemic cure for smokers, in a further embodiment of the invention nicotine is present in the single dosage topical pharmaceutical form.

To improve the handling of the single dosage topical pharmaceutical form further in practice, in a further embodiment of the invention, on the moulded body serving as a common pack, appropriate positions of the topical individual dosages in a treatment scheme are marked with numerical, coloured or symbolic information and instructions.

To improve the administration of the single dosage topical pharmaceutical form further in practice, in a further embodiment of the invention therapeutic single doses for various therapy phases are separately detachable from the commercial moulded body serving as a common pack.

The advantages achieved by the invention are in particular that the known therapeutic advantages of transdermal administration can be assumed, e.g. decreased systemic hepatic first pass effect, but at the same time the previous inaccuracy of customary topical pharmaceutical forms is significantly reduced.

Thus, in a laboratory investigation with 50 manual individual withdrawals from prefilled blister chambers for an oestrogen-containing formulation at an individual filling amount of 0.5 gram, a withdrawal accuracy of the topical formulation with a relative standard deviation of 1.9% could be reproduced (FIG. 1). This lies significantly below the limit of 5% demanded of pharmaceuticals on the part of GMP procedure. In contrast, on measurement of the reproducibility of the withdrawal for a conventional topical gel formulation containing oestrogen from a customary tube a relative standard deviation of over 15% was found.

The single dosage topical pharmaceutical form moreover makes possible an individualised and variable procedure. It enables prefinished exact dosage changes and also prefinished and exactly dosed combinations. By this means, in its commercial application it also stands in a greater analogy to the procedure in the case of oral administration forms.

The defined total ratios of the single dosage topical pharmaceutical form which result from the specified physicochemical characteristics of the pharmaceutical form, e.g. physical spreading behaviour on the skin and permeation into the skin, the exact topical individual dose and the given prescription scheme, make possible a significantly more exact effect control, and thus also distinctly higher therapeutic safety than previously, compared to customary topical administrations.

Moreover, the single dosage topical pharmaceutical form is also distinctly more hygienic and can be protected better against microbial effects, both with respect to administration itself and with respect to its storage conditions.

Compared with transdermal plasters, the single dosage topical pharmaceutical form is very inexpensive, which results in particular also from its low formulation costs in mass production. It can moreover be prepared with customary pharmaceutical agents and also under all customary production precautions, e.g. aseptic or sterile preparation, and also with suitable stability.

Compared with commercial transdermal systems, the skin tolerability of the single dosage topical pharmaceutical form is fundamentally better.

Modifications of the single dosage topical pharmaceutical form are programmable by means of the type and embodiment of a treatment scheme which can be fixed to the commercial container, for example different dosages and also active compound combinations being possible at the same time, e.g. of oestrogens and oestrogen-gestagen combinations.

By variations in the distributions of the crystal sizes of the active compound contained in the topical pharmaceutical formulations, different pharmacokinetic profiles, e.g. delayed-release effects, can also be produced by the different permeation and depot behaviour resulting therefrom.

The exemplary embodiment of a treatment pack based on the invention, in this case for a single dosage topical administration for hormone replacement in the case of post-menopausal symptoms, may be mentioned. This example is only intended to illustrate the invention without restricting it thereto. It primarily serves the purpose of presenting a therapeutic possibility and also the degree of specificity which can be achieved with single dosage topical pharmaceutical forms in a transdermal systemic therapy.

EXAMPLE

The topical treatment pack consists of a moulded body made of blister material customary for pharmaceutical purposes serving as the pack pack. An individual moulded body in this case contains 14 hemispherically-shaped chambers serving as individual containers for topical individual doses. These can admit filling materials in the range from 0.1 to 1 gram. The treatment pack for one month in this case comprises 2 of these blister packs in each case having 14 chambers for a 28-day treatment with a daily individual dose. The ready-to-administer therapeutic individual doses of the formulation containing 0.5 gram are situated in the chambers. The individual chambers are numbered continuously from 1 to 28. The blister pack 1 with the chambers 1–14 in this case contains in 0.5 gram in each case of topical vehicle 3 mg in each case of the oestrogen 17β-estradiol; the blister 2 with the chambers 15–28 in this case contains in 0.5 gram in each case of topical vehicle a combination of 3 mg of the oestrogen 17β-estradiol and 1 mg of the gestagen norethisterone acetate.

BRIEF DESCRIPTION OF DRAWINGS

The following drawings are illustrative of embodiments of the invention and are not meant to limit the scope of the invention as encompassed by the claims.

Figure 1:
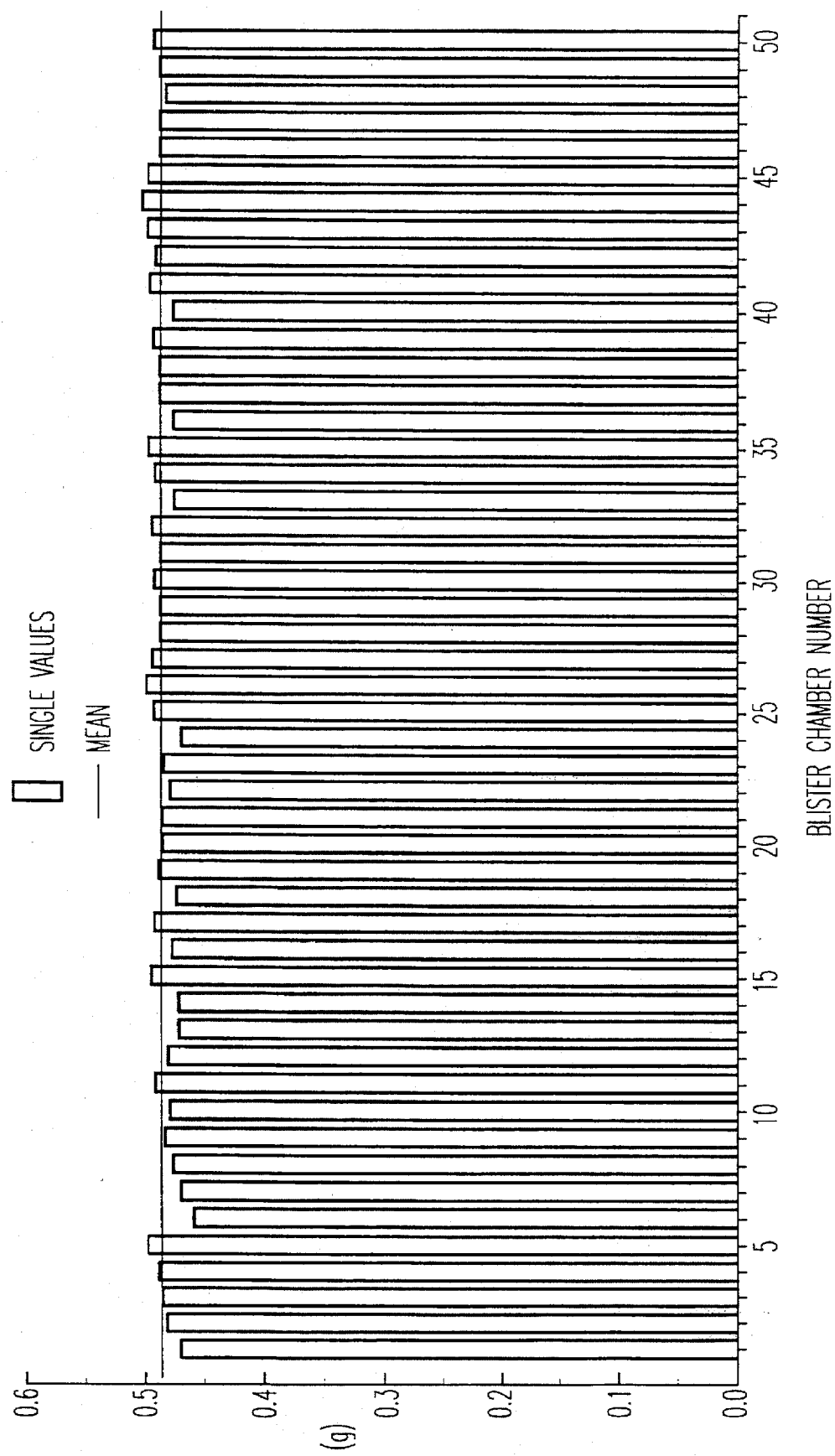
FIG. 1 graphically shows a comparison of the accuracy of single dosage form blisters.
Figure 2:
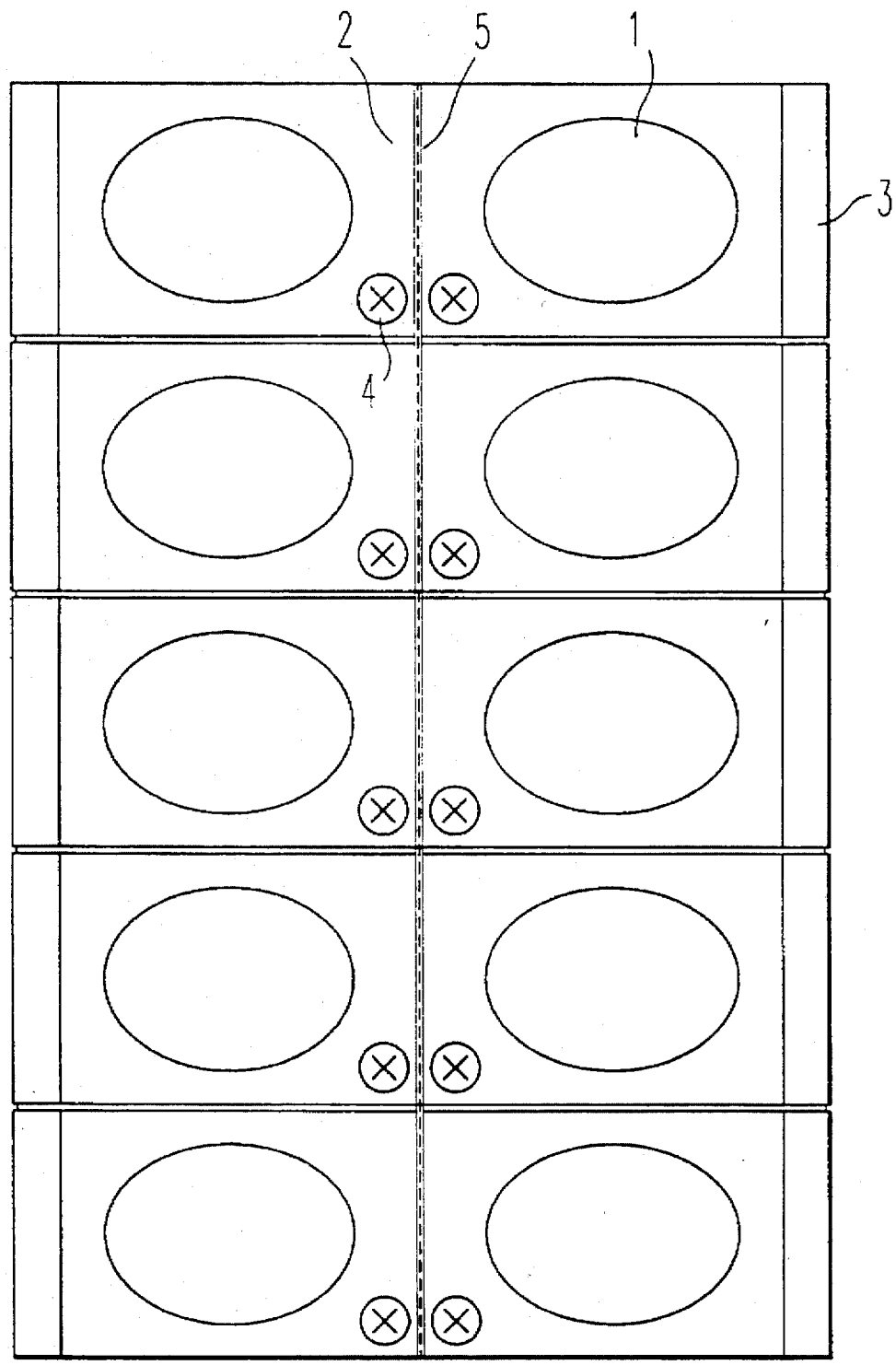
FIG. 2 illustrates the cutaway view of a treatment pack, with topical individual dosage forms.

The cutaway view of a treatment pack with topical individual dosages is shown for further illustration in FIG. 2, this representation only illustrating the pack without restricting it, however, in its further embodiment.

The individual blister chambers of the treatment pack (1), which contain the topical individual doses, are sealed in an air-tight manner on their tops with a peel-off foil (2) of aluminium. The peel-off foils are in this case attached such that they have flaps (3) on their outer side using which each chamber for an individual dose can also be individually opened. The covering foil can in this case be provided in various positions with figures (4) for each day or alternatively additionally with colour codes for the type of treatment phase. The treatment pack is provided with perforations (5) which enable individual doses to be detached from the complete pack in unopened form.

The therapeutic individual doses contained in the individual chambers are withdrawn daily, also as in a tablet administration scheme, and directly applied to the skin. On account of the specified spreading behaviour of the vehicle, a statistically average skin surface coating also results in this case.

The coating volume of the individual dose containers and the statistically average withdrawal residue is checked in production and taken into account according to production.

Figure 3:
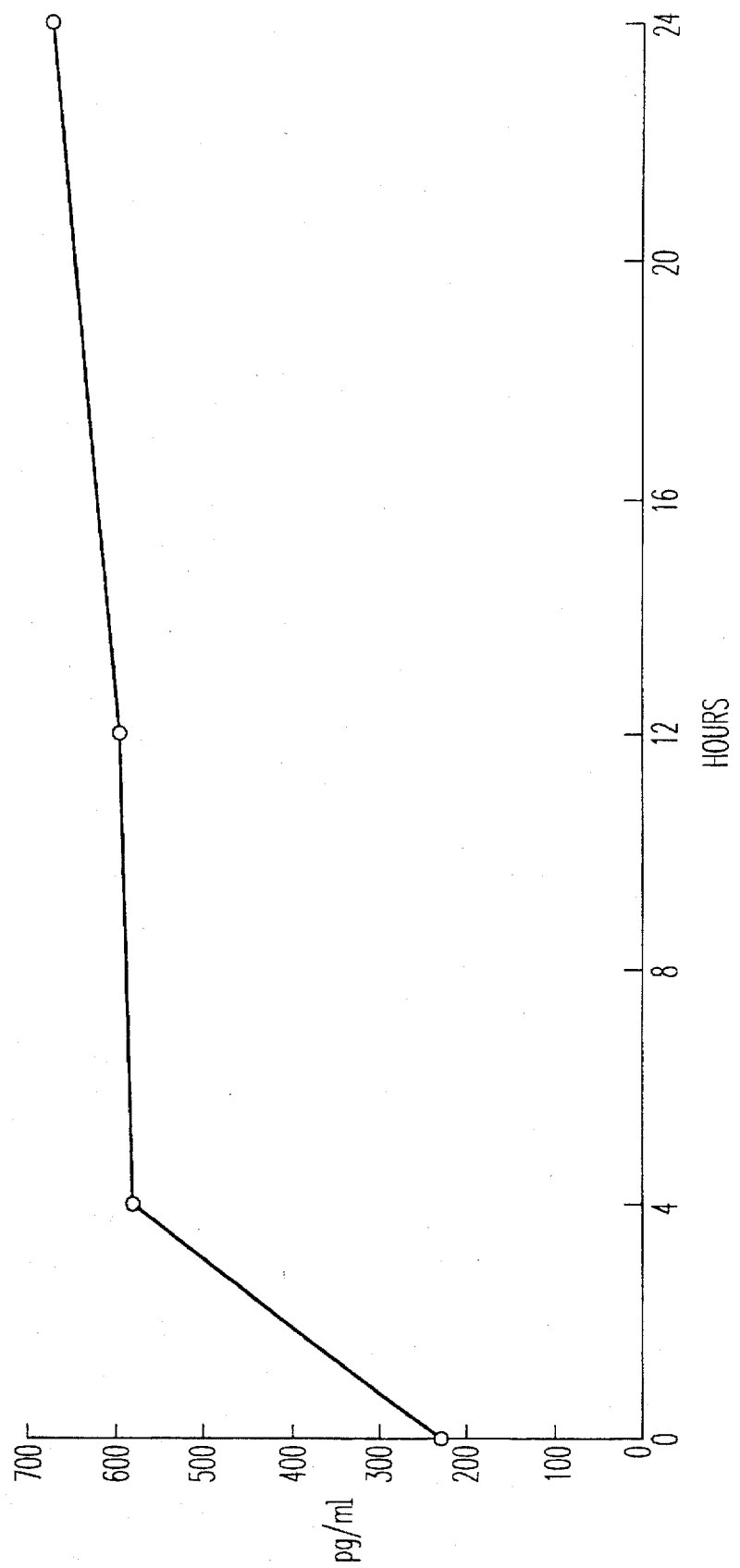
FIG. 3 represents the mean estrogen serum concentration after single dose application.

Using a single dosage topical pharmaceutical form, a clinical pilot test was carried out on 4 subjects using an oestrogen, estriol. The result is shown in FIG. 3. The latter represents the average course of the serum concentration of radioimmunologically measured total estriol over a period of 24 hours after topical application. It turns out from this that, with an individual topical dosage, an increased level of steroid hormone lasting for over 24 hours can be achieved on the skin.

I claim:

1. A molded body, comprising a plurality of separate, measured and detachable dosages, wherein each of said dosages contains a single dosaage, ready-to administer semi-solid phase formulation for transdermal therapy.

2. The molded body of claim 1, wherein said pharmaceutical formulation is in creme, emulsion, gel, suspension or ointment form.

3. The molded body of claim 1, wherein said separate chambers are individually air-tightly sealed with a peel-off foil such that each separate chamber can be opened individually.

4. The molded body of claim 1, wherein said single dosage formulation comprises a pharmaceutical vehicle and an active compound.

5. The molded body of claim 4, wherein said active compound has a uniform average crystal size or a mixture of various crystal sizes.

6. The molded body of claim 4, wherein said active compound comprises estrogens, gestogens, glucocorticoids or mixtures thereof.

7. The molded body of claim 4, wherein said active compound comprises a pharmacologically active peptide, protein or mixture thereof.

8. The molded body of claim 4, wherein said active compound comprises insulin, oxytocin, encephalins and mixtures thereof.

9. The molded body of claim 4, wherein said active compound is selected from the group consisting of analgesics, local anesthetics and mixtures thereof.

10. The molded body of claim 4, wherein said active compound comprises buprenorphine, fentanyl, penzocaine, morphine, lidocaine, prilocaine, mepivacaine and mixtures thereof.

11. The molded body of claim 4, wherein said active compound comprises antirheumatics, antiinflammatories or mixtures thereof.

12. The molded body of claim 4, wherein said active compound comprises indomethacin, diclofenac, etofenamate or mixtures thereof.

13. The molded body of claim 4, wherein said active compound comprises nicotine.

14. The molded body of claim 4, wherein said separate chambers are marked with numerical, colored or symbolic information or instructions relating to a therapeutic treatment scheme.

15. The molded body of claim 4, wherein said active compound is a morphine derivative.

* * * * *